(12) United States Patent
Barletta et al.

(10) Patent No.: US 7,740,867 B2
(45) Date of Patent: Jun. 22, 2010

(54) METHOD FOR IDENTIFICATION OF VIRULENCE DETERMINANTS

(75) Inventors: Raul G. Barletta, Lincoln, NE (US); N. Beth Harris, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 11/945,770

(22) Filed: Nov. 27, 2007

(65) Prior Publication Data

US 2008/0166321 A1 Jul. 10, 2008

Related U.S. Application Data

(62) Division of application No. 09/759,287, filed on Jan. 11, 2001, now abandoned.

(60) Provisional application No. 60/175,433, filed on Jan. 11, 2000.

(51) Int. Cl.
*A61K 39/02* (2006.01)
*A61K 39/04* (2006.01)
*A61K 49/00* (2006.01)

(52) U.S. Cl. .................. 424/234.1; 424/9.1; 424/9.2; 424/93.1; 424/93.2; 424/184.1; 424/248.1; 424/278.1; 424/823; 435/220.1; 435/440; 435/441; 435/442; 435/444; 435/466; 435/866; 514/2

(58) Field of Classification Search .................. 424/9.1, 424/9.2, 93.1, 93.2, 184.1, 234.1, 248.1, 424/278.1, 823; 435/220.1, 440, 441, 442, 435/443, 444, 466, 866; 514/2
See application file for complete search history.

(56) References Cited

U.S. PATENT DOCUMENTS

| | | | |
|---|---|---|---|
| 4,341,761 A | 7/1982 | Ganfield et al. |
| 4,399,121 A | 8/1983 | Albarella et al. |
| 4,427,783 A | 1/1984 | Newman et al. |
| 4,444,887 A | 4/1984 | Hoffmann |
| 4,466,917 A | 8/1984 | Nussenzweig et al. |
| 4,472,500 A | 9/1984 | Milstein et al. |
| 4,491,632 A | 1/1985 | Wands et al. |
| 4,493,890 A | 1/1985 | Morris |
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,783,386 A | 7/1998 | Jacobs, Jr. et al. |
| 6,095,549 A | 8/2000 | Pelicic et al. |

FOREIGN PATENT DOCUMENTS

| | | |
|---|---|---|
| EP | 0 812 918 A2 | 12/1997 |
| WO | WO 92/22326 A1 | 12/1992 |
| WO | WO 95/03417 A2 | 2/1995 |
| WO | WO 99/02670 A1 | 1/1999 |
| WO | WO 99/05168 A1 | 2/1999 |
| WO | WO 99/10475 A2 | 3/1999 |

OTHER PUBLICATIONS

Woo, S-R., et al. ATP release by infected bovine monocytes increases the intracellular survival of *Mycobacterium avium subsp, paratuberculosis.* Comp Immunol Microbiol Infect Dis (2008), doi:10.1016/j.cimid.2007.11.003.
Woo, S-R., et al. Life and death in bovine monocytes: the fate of *Mycobacterium avium subsp. paratuberculosis.* Microbial Pathogenesis 43 (2007) 106-113.
Woo, S-R., et al. Bovine monocytes and a macrophage cell line differ in their ability to phagocytose and support the intracellularr survival of *Mycobacterium avium subsp. paratuberculosis.* Vet. Immunol. Immunpathol 110 (2006) 109-120s.
Woo, S-R., et al.. Extracellular ATP Is Cytotoxic to Mononuclear Phagocytes but Does Not Induce Killing of Intracellular *Mycobacterium avium subsp. paratuberculosis.* Clin Vaccine Immunol 14:9 (2007) 1078-1083.
Balasubramanian et al., Allelic Exchange in *Mycobacterium tuberculosis* with Long Linear Recombination Substrates, *J. Bacter.*, Jan. 1996, pp. 273-79, vol, 178, No. 1, Amer. Soc, Microb., USA.
Bardarov et al., Conditionally replicating mycobacteriophages: A system for transposon delivery to *Mycobacterium tuberculosis, Proc. Natl. Acad. Sci.*, Sep. 1997, pp. 10961-10966, vol. 94, Natl. Acad. Sci., USA.
Beaucage et al., Deoxynucleoside Phosphoramidites-A New Class Of Key Intermediates For Deoxypolycucleotide Synthesis, *Tet. Let.*, 1981, pp. 1859-1862, vol. 22, No. 20.
Bermudez et al., Isolation of two subpopulations of *Mycobacterium avium* within human microphages, *FEMS Micro. Let.*, p. 19-26, vol. 178, Elsevier Sciences.
Cáceres et al., Overexpression of the D-Alanine Racemase Gene Confers Resistance to D-Cycloserine in *Mycobacterium smegmatis, J. Bacter.*, Aug. 1997, pp. 5046-5055, vol. 179, No. 16, Amer. Soc. Micro., USA.
Camphausen et al., A glycolipid antigen specific to *Mycobacterium paratuberculosis*: Structure and antigenicity, *Proc. Natl. Acad. Sci.*, May 1985, pp. 3068-3072, vol. 82.
Cavaignac et al., Construction and screening of *Mycobacterium paratuberculosis* insertional mutant libraries, *Arch. Microbiol.*, 2000, pp. 229-231, vol. 173.
Cirillo et al., A Novel Transposon Trap for Mycobacteria: Isolation and Characterization of IS1096, *J. Bacter.*, Dec. 1991, pp. 7772-7780, vol. 173, Amer. Soc. Microb., USA.
Cirillo et al., Interaction of *Mycobacterium avium* with Environmental Amoebae Enhances Virulence, *Infec. and Immun.*, Sep. 1997, pp. 3759-3767, vol. 65, No. 9, Amer. Soc. Microb., USA.
Cocito et al., Paratuberculosis, *Clin. Microb. Reviews*, Jul. 1994, pp. 328-345, vol. 7, No. 3, Amer. Soc. Microb., USA.
Collins, Paratuberculosis diagnostics; We created the tests, now how do we use them?, *Proc. Fifth Intl. Colloq. Paratuberculosis*, Chiodini et al., eds., Intl. Assoc. for Paratuberculosis, 1997, pp. 232-241.

(Continued)

*Primary Examiner*—Rodney P. Swartz
(74) *Attorney, Agent, or Firm*—Stinson Morrison Hecker LLP

(57) ABSTRACT

Disclosed are methods for the determination of virulence determinants in bacteria and in particular bacteria of the genus *Mycobacterium*. Also disclosed are compositions and methods for stimulating an immune response in an animal using bacteria and virulence determinants identified by the methods of the present invention.

10 Claims, 2 Drawing Sheets

OTHER PUBLICATIONS

Collins et al., Herd prevalence and geographic distribution of, and risk factors for, bovine paratuberculosis in Wisconsin, J. Amer. Vet. Med. Assoc., Feb. 1994, pp. 636-641, vol. 204, No. 4.

Ellingson et al., Identification of a gene unique to *Mycobacterium avium subspecies paratuberculosis* and application to diagnosis of paratuberculosis, *Mol. Cell. Probes*, 1998, pp. 133-142, vol. 12, Academic Press, USA.

El-Zaatari et al., Characterization of a Specific *Mycobacterium paratuberculosis* Recombinant Clone Expressing 35,000-Molecular-Weight Antigen and Reactivity, with Sera from Animals with Clinical and Subclinical Johne's Dsease, *J. Clin. Microb.*, Jul. 1997, pp. 1794-1799, vol. 35, No. 7, Amer. Soc. Microb., USA.

Foley-Thomas et al., Phage infection, transfection and transformation of *Mycobacterium* avium complex and *Mycobacterium paratuberculosis*, 1995, pp. 1173-1181, vol. 141.

Green et al., Sequence and characteristcs of IS900, an insertion element identified in a human Crohn's disease Isolate of *Mycobacterium paratuberculosis, Nucl., Acids. Res*, 1989, pp, 9063-9073, vol. 17, No. 22, IRL Press.

Guateli et al., Isothermal, in vitro amplification of nucleic acids by a multienzyme reaction modeled after refroviral replication, *Proc. Natl. Acad. Sci.*, Mar. 1990, pp. 1874-1878, vol. 87, Biochem., USA.

Guilhot et al., Efficient Transposition in *Mycobacteria*: Construction of *Mycobacterium smegmatis* Insertional Mutant Libraries, Jan. 1994, pp. 535-539, vol. 176, No. 2, Amer. Soc. Microb., USA.

Gunnarsson et al., Analysis of Antigens in Mycobacterium Paratuberculosis, *Acta. Vet. Scand.*, 1979, pp. 201-215, vol. 20.

Hamilton et al., *Mycobacterium paratuberculosis* Monoassociated Nude Mice as a Paratuberculosis Model, *Vet. Pathol.*, 1991, pp. 146-155, No. 28.

Homuth et al., Identification and Characterization of a Novel Extracellular Ferric Reductase from *Mycobacterium paratuberculosis, Inf. & Immun.*, Feb. 1998, pp. 710-716, vol. 66, No. 2, Amer. Soc. Microb., USA.

Hseih et al., Two-dimensional electrophoretic analysis of *Mycobacterium avium* and *M. paratuberculosis* iron-regulated proteins, *Proc. Fifth Intl. Paratuberculosis*, pp. 82-87.

Jacobs, Jr. et al., Genetic Systems for *Mycobacteria, Meth. Enzy.*, 1991, pp. 537-555, vol. 204, Academic Press, USA.

Kwoh et al., Transcription-based amplification system and detection of amplified human immunodeficiency virus type 1 with a bead-based sandwich hybridization format, *Pro. Natl. Acad. Sci.*, Feb. 1989, pp. 1173-1177, vol. 86, Biochem., USA.

Landegren et al., A Ligase-Mediated Gene Detection Technique, *Science*, Aug. 1988, pp. 1077-1080, vol. 241.

Martin et al., Transposition of an antibiotic resistance element in mycobacteria, *Nature*, Jun. 1990, pp. 739-743, vol. 345.

McAdam et al., In Vivo Growth Characteristics of Leucine and Methionine Auxotrophic Mutants of *Mycobacterium bovis* BCG Generated by Transposon Mutagenesis, *Inf. and Immun.*, Mar. 1995, pp. 1004-1012, vol. 63, No. 3, Amer. Soc. Microb., USA.

Mutharia et al., Analysis of Culture Filtrate and Cell Wall-Associated Antigens of *Mycobacterium Paratuberculosis* with Monoclonal Antibodies, *Inf. and Immun.*, Feb. 1997, pp. 387-394, vol. 65, No. 2, Amer. Soc. Microb., USA.

Pelicic et al., Efficient allelic exchange and transposon mutagenesis in *Mycobacerium tuberculosis, Proc. Natl. acad. Sci.*, Sep. 1997, pp. 10955-10960, vol. 94.

Pelicic et al., Genetic advances for studying *Mycobacterium Tuberculosis* pathogenicity, *Mol. Microb.*, 1998, pp. 413-420, vol. 28, No. 3.

Shapiro-Hurley et al., Deoxyribonucleic Acid Relatedness of *Mycobacterium paratuberculosis* to Other members of the Family *Mycobacteriaceae, Intl. J. Syst. Bacteriol.*, Apr. 1988, pp. 143-146, vol. 38, No. 2, Intl. Union Microb. Soc.

St-Jean et al., Treatment of *Mycobacterium paratuberculosis* Infection in Ruminants, *Vet. Clin. N. Am. Food Anim. Prac.*, Nov. 1991, pp. 793-805, vol. 7, No. 3.

St-Jean, Treatment Of Clinical Paratuberculosis In Cattle, *Vet. Clin. N. Am. Food Anim. Prod.*, Jul. 1996, pp. 417-430, vol. 12, No. 2.

Stabel, An improved method for cultivation of *Mycobacterium paratuberculosis* from bovine fecal samples and comparison to three other methods, *J. Vet. Diagn. Invest.*, 1997, pp. 375-380, vol. 9.

Stevenson, The Contribution of Molecular Biology to *Mycobacterium avium Subspecies paratuberculosis* Research, *Vet. Jour.*, 1997, pp. 269-286, vol. 153.

Sugden et al., Chromatographic Purification and Characterization of Antigens A and D from *Mycobacterium paratuberculosis* and Their Use in Enzyme-Linked Immunosorbent Assays for Diagnosis of *Paratuberculosis* in Sheep, *Jour. Clin. Microb.*, Aug. 1991, pp. 1659-1664, vol. 29, No. 8, Amer. Soc. Microb., USA.

Thorel et al., Numerical Taxonomy of Mycobactin-Dependent *Mycobacteria*. Amended Description of *Mycobacterium avium*, and Description of *Mycobacterium avium subsp. avium* subsp, nov., *Mycobacterium avium subsp. paratuberculosis* subsp. nov., and *Mycobacterium avium subsp. silvaticum* subsp. nov., *Int. J. System. Bacteriol.*, Jul. 1990, pp. 254-260, vol. 40, No. 3, Inter. Union Microb. Soc.

Van Schaik et al., Cost-benefit analysis of vaccination against *paratuberculosis* in dairy cattle, *Vet. Rec.*, Dec. 1996, pp. 624-627, vol. 139.

Whipple et al., Development of the beige mouse as an animal model for *M. paratuberculosis* infection, *Proc. 3rd Intl. Colloq. Paratuberculosis*, pp. 551-552.

White et al., Comparison of cellular and extracellular proteins expressed by various isolates of *Mycobacterium paratuberculosis* and other mycobacterial species, *Am. J. Vet. Res.*, Oct. 1994, pp. 1399-1405, vol. 55, No. 10.

Williams et al., Development of a Firefly Luciferase-Based Assay for Determining Antimicrobial Susceptibility of *Mycobacterium avium subsp. paratuberculosis, J. Clin. Microb.*, Feb. 1999, pp. 304-309, vol. 37, No. 2, Amer. Soc. Microb., USA.

Wu et al., The Ligation Amplification Reaction (LAR)-Amplification of Specific DNA Sequences Using Sequential Rounds of Template-Dependent Ligation, *Genomics*, 1989, pp. 560-569, vol. 4.

Coulter, S.N. et al., "*Staphylococcus aureus* Genetic Loci Impacting Growth and Survival in Multiple Infection Environments", Molecular Microbiology, Oct. 1998, pp. 393-404, vol. 30, No. 2.

Darwin, A.J. et al., "Identification of Yersinia enterocolitica Genes Affecting Survival in an Animal Host Using Signature-tagged Transposon Mutagenesis", Molecular Microbiology, Apr. 1999, pp. 51-62, vol. 32, No. 1.

Hensel, M. et al., "Simultaneous Identification of bacterial Virulence Genes by Negative Selection", Science, Jul. 1995, pp. 400-403, vol. 269.

Perry, R.D., "Signature tagged Mutagenesis and the Hunt for Virulence Factors", Trends in Microbiology, Oct. 1999, pp. 385-388, vol. 7, No. 10.

Ramaswamy, S. et al., "Molecular genetic Basis of Antimicrobial Agent Resistance in Mycobacterium Tuberculosis: 1998 Update", Tubercle and Lung Disease: The Official Journal of the International Union Against Tuberculosis and Lung Disease, 1998, pp. 3-29, vol. 79, No. 1, Scotland.

Tang, C. et al., "Pathogen Virulence Genes—Implications for Vaccines and Drug Therapy", British Medical Bulletin, 1999, pp. 387-400, vol. 55, No. 2, England.

International Search Report, PCT/US01/00980.

Amsterdam, D., Susceptibility Testing of Antimicrobials in Liquid Media, in Antibiotics in Laboratory Medicine, 4th ed., 1996, pp. 52-111, Williams and Wilkins, Baltimore, MD (Lorian, V., ed.).

Eisenstadt, et al., Gene Mutation, *in* Methods for General and Molecular Bacteriology, 1994, pp, 297-316, ASM Press, Washington D.C, (Gerhardt, et al., eds.).

Rest, R.F. and Speert, D.P Measurement of Nonosponic Phagocytic Killing by Human and Mouse Phagocytes, *in* Bacterial Pathogenesis, 1997, pp. 475-492, Academic Press, San Diego, CA (Clark and Bavoli, eds.).

| GPM207 | 7 | RRTGPVGISAVAALHGWSDSGQP | 75 |
| --- | --- | --- | --- |
| | | +RT P G+ A  AL GW D G+P | |
| XerC (M. leprae) | 181 | QRTAPFGVPAADALRGWLDDGRP | 203 |

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
ggtcagcgca ggcgaagccc                                                 20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
gccaggtcca cactgccccc                                                 20

<210> SEQ ID NO 3
<211> LENGTH: 19
<212> TYPE: DNA
<213> ORGANISM: Mycobacterium smegmatis
<220> FEATURE:
<221> NAME/KEY: misc_feature
<222> LOCATION: (1)..(19)
<223> OTHER INFORMATION: Transposon

<400> SEQUENCE: 3
tgttaacggg ctcttcgca                                                  19

<210> SEQ ID NO 4
<211> LENGTH: 19
<212> TYPE: DNA
<213> ORGANISM: Mycobacterium smegmatis
<220> FEATURE:
<221> NAME/KEY: misc_feature
<222> LOCATION: (1)..(19)
<223> OTHER INFORMATION: Transposon

<400> SEQUENCE: 4
tgcgaagagc ctgttaacg                                                  19

<210> SEQ ID NO 5
<211> LENGTH: 23
<212> TYPE: PRT
<213> ORGANISM: Mycobacterium paratuberculosis
```

```
-continued

<400> SEQUENCE: 5

Arg Arg Thr Gly Pro Val Gly Ile Ser Ala Val Ala Ala Leu His Gly
1               5                   10                  15

Trp Ser Asp Ser Gly Gln Pro
            20

<210> SEQ ID NO 6
<211> LENGTH: 23
<212> TYPE: PRT
<213> ORGANISM: Mycobacterium leprae

<400> SEQUENCE: 6

Gln Arg Thr Ala Pro Phe Gly Val Pro Ala Ala Asp Ala Leu Arg Gly
1               5                   10                  15

Trp Leu Asp Asp Gly Arg Pro
            20
```

METHOD FOR IDENTIFICATION OF VIRULENCE DETERMINANTS

CROSS-REFERENCE TO RELATED APPLICATIONS

This application is a divisional of U.S. patent application Ser. No. 09/759,287, filed Jan. 11, 2001, which claims the benefit of provisional application 60/175,433 filed Jan. 11, 2000, the disclosures of which are hereby incorporated by reference in their entirety for all purposes.

STATEMENT REGARDING FEDERALLY SPONSORED RESEARCH OR DEVELOPMENT

This invention was made with government funds under 98-35204-6761 and 99-35204-7789 awarded by United States Department of Agriculture/CSREES. The U.S. Government has rights in this invention.

BACKGROUND OF THE INVENTION

Paratuberculosis (Johne's disease) is an incurable, fatal disease of domestic and wild ruminants. *Mycobacterium paratuberculosis* (*M. paratuberculosis*) is the etiologic agent of this disease. *Mycobacterium avium* (*M. avium*) and *M. paratuberculosis* are slow-growing faculative intracellular mycobacteria able to grow in mononuclear phagocytes. DNA-DNA hybridization studies have shown that these micro-organisms belong to a single genomic species (Hurley et al., *Intl. J. Syst. Bacteriol.*, 38:143-146, 1988), and it has been proposed to reclassify *M. paratuberculosis* as a subspecies of *M. avium* (Thorel et al., *Intl. J. Syst. Bacteriol.* 40:254-260, 1990). Furthermore, all *M. paratuberculosis* strains are characterized by the presence of the insertion sequence IS900 (Green et al., *Nucleic Acids Res.*, 17:9063-9073, 1989), which is absent from most *M. avium* strains. Phenotypic differences between *M. avium* and *M. paratuberculosis*, such as mycobactin requirement, ability to grow on egg medium, growth stimulation by pyruvate, and tolerance to cycloserine correlate with variations in pathogenicity and host range (Thorel et al., *Intl. J. Syst. Bacteriol.* 40:254-260, 1990).

Johne's disease is manifested by chronic diarrhea and weight loss. After months of diarrhea and wasting, the affected animals either die or are culled. In the United States, the prevalence of *M. paratuberculosis* infection in dairy and beef cattle herds has reached 34% in certain areas (Collins et al., *J. Am. Vet. Med. Assn.* 187:323-329, 1992; Collins et al., *J. Am. Vet. Med. Assn.* 204:636-641, 1994) and results in millions of dollars in lost revenues annually. Furthermore, *M. paratuberculosis* has been tentatively linked to Crohn's disease, a chronic granulomatous ileitis in humans. Evidence supporting the possibility that *M. paratuberculosis* is the etiologic agent of Crohn's disease includes culture of *M. paratuberculosis* is from intestinal tissue, and amplification by PCR of the subspecies-specific IS900 sequence of *M. paratuberculosis* from biopsy specimens.

Natural infection in cattle is usually acquired in the first months of life. The age of onset of clinical Johne's disease varies, being most frequent during or after the second lactation in dairy cattle. The prolonged incubation time and the difficulty in diagnosing subclinical cases facilitate the insidious spread of the infection within a herd. Bacteriologic culture is the most definitive diagnostic method, but requires substantial time and labor (Stabel, *J. Vet. Diag. Invest.*, 9:375-380, 1997), and it is unable to detect infected animals that do not shed acid-fast bacilli. Progress has been made by combining fecal culture, PCR detection (IS900), and tests for humoral (ELISA) or cellular immunity (IFN-γ test) (Collins, *Proceedings of the Fifth Intl. Colloq. Paratuberculosis*, Chiodini et al., eds., Intl. Assn. for Paratuberculosis, 1997, pp. 232-241.). More recently, a gene unique to *M. paratuberculosis* (hspX) was identified and has promise as a new diagnostic tool (Ellingson et al., *Mol. Cell Probes* 12:133-142, 1998).

Currently, treatment of paratuberculosis in cattle is limited to the extra label use of therapeutic agents (St.-Jean et al., *Vet. Clin. N. Am. Food Anim. Pract.*, 7:793-804, 1991; St.-Jean, *Vet. Clin. N. Am. Food Anim. Pract.*, 12:417-430, 1996), and no antibiotic treatment is recommended for clinical cases of Crohn's disease. Even with a prolonged drug regimen paratuberculosis in cattle is invariably fatal.

Little is known about *M. paratuberculosis* immunogens and virulence determinants (Cocito et al., *Clin. Microbiol. Rev.* 7:328-345, 1994). Lipoarabinoman (Sugden et al., *J. Clin. Microbiol.*, 29:1659-1664, 1991), glycopeptidolipid 1 (Camphausen et al., *Proc. Natl. Acad. Sci. USA*, 82:3068-3072, 1985), and 35 kDa (p35) antigen (El Zaatari et al., *J. Clin. Microbiol.*, 35:1794-1799, 1997) are three major immunogens. Antigen p35 was recognized by sera from all clinically diseased cattle and by fifteen out of twenty cattle with subclinical diseases. This antigen, however, is not specific for paratuberculosis, since it is widely present in other strains of the *M. avium* complex. Several protein antigens have been identified by two-dimensional immunoelectrophoresis with hyperimmune sera, but only a subset of these antigens are recognized by sera from animals with paratuberculosis (Gunnarsson and Fedstand, *Acta Vet. Scand.* 20:200-215, 1979). Comparison of the two-dimensional gel electrophoretic profiles of *M. paratuberculosis* and *M. avium* cells grown in Middlebrook 7H9 medium followed by Western blot analysis, using antiserum from clinically infected cows, revealed a 42 kDa protein which may be specific for *M. paratuberculosis* (White et al., *Am. J. Vet. Res.*, 55:1399-1405, 1994). Using the same methodology, AHPC gene products were identified that may be antigenic (Hsieh et al., *Proceed. Fifth Intl. Colloq. Paratuberculosis*, Chiodini et al., eds., 1997, pp. 82-87).

*M. paratuberculosis* antigens that have been cloned include the heat shock proteins HSP65 and HSP70, the transposase form IS900, a putative serine protease, bacterioferritin, the 34 kDa antigen bearing major B cell epitopes (reviewed by Stevenson and Sharp, *Vet. J.* 153:269-286, 1997), and more recently, the 35 kDa antigen (El Zaatari et al., *J. Clin. Microbiol.* 35:1794-1799, 1997) and the fled protein from IS900 (Doran et al., *Microbiol.* 143:547-552, 1997). In addition, a novel extracellular ferric reductase enzyme activity with a potential role in the evasion of intracellular defense mechanisms has been identified (Homuth et al. *Infect. Immun.*, 66:710-716, 1998). Secreted proteins of *M. paratuberculosis* have received attention as potential immune targets early in infection. Some of these proteins are present as glyconjugates and different epitopes in the glycosylated and non-glycosylated moieties seem to be recognized in cattle and sheep (Mutharia et al, *Infect. Immun.* 65:387-394, 1997).

Diagnosis and control of paratuberculosis presents a significant challenge. Although vaccination does reduce clinical signs of Johne's disease, it does not prevent losses in milk production (van Schaik et al., *Vet. Rec.*, 139:624-627, 1996). Improved vaccines and diagnostic tools are urgently needed. Likewise faster, specific, and more accurate and sensitive diagnostics need to be developed, especially to detect animals in the early stages of the disease. These tools preferably should also be able to discriminate between vaccinated and infected animals.

Identification of *M. paratuberculosis* virulence determinants is a critical step in developing suitable methods of diagnosis and control, and requires a systematic method by which virulence determinants can be found. U.S. Pat. No. 5,783,386 to Jacobs et al. describes a method for identifying virulence determinants of mycobacterial species involving the preparation of a genomic DNA library and constructing shuttle vectors containing inserts from the library constructed. These vectors are then used to transform a virulent organisms to form recombinants. Virulence determinants are identified by inoculating animals with the transformed recombinant organisms to select virulent recombinants and then identifying the DNA sequences that confer virulence. Cavaignac, et al. (*Arch. Microbial.* 173:229-231, 2000) studied virulence mechanisms in *M. paratuberculosis* by the introduction of random mutants using transposon mutagenesis. Two thousand mutants were screened on the basis of auxotrophy and altered cell wall. Pelicic et al. (U.S. Pat. No. 6,096,549) disclose a method for inserting a transposon into a *mycobacterium* strain using a vector containing the sacB gene. Use of this vector to identify virulence determinants is also disclosed. The present disclosure teaches an alternative method utilizing transposon mediated mutation and positive selection of mutants by antimicrobial agents that kill growing mycobacteria.

BRIEF SUMMARY OF THE INVENTION

Among the several aspects of the invention is provided a method for identifying virulence determinants of a bacteria comprising introducing at least one mutation into the genome of a bacteria; culturing the mutated bacteria in the presence of an antimicrobial agent that kills growing but not non-growing bacteria; selecting surviving bacteria; testing the selected surviving bacteria for virulence; selecting the non virulent bacteria; sequencing genetic material from the selected non virulent bacteria; determining the site of mutation; and comparing the sequence at the mutated site to the corresponding wild type sequence.

Another aspect provides a composition for immunizing an animal against bacterial infection comprising a pharmaceutically acceptable carrier, diluent or excipient; and at least one non-virulent strain of bacteria produced by the process comprising introducing at least one mutation into the genome of a bacteria; culturing the mutated bacteria in the presence of an antimicrobial agent that kills growing but not non-growing bacteria; selecting surviving bacteria; testing the selected surviving bacteria for virulence; and selecting the non-virulent strains.

Still another aspect provides a composition for immunizing an animal against a bacteria comprising a pharmaceutically acceptable carrier diluent or excipient; and at least one bacterial virulence determinant, the determinant identified by a process comprising; introducing at least one mutation into the genome of a bacteria; culturing the mutated bacteria in the presence of an antimicrobial agent that kills growing but not non-growing bacteria; selecting surviving bacteria; testing the selected surviving bacteria for virulence; selecting the non-virulent strains; sequencing genetic material from the selected non-virulent bacteria to determine the site of the mutation; and identifying the virulence determinant based on the site of the mutation.

Yet another aspect provides a method for inducing an immune response in an animal against a bacteria comprising administering to an animal an immune response inducing amount of any of the previously described compositions.

Another aspect provides a method for diagnosing infection by *Mycobacterium paratuberculosis* comprising obtaining a sample from an animal and determining the presence or absence in the sample of a bacterial virulence determinant, said determinant identified by the methods described above.

BRIEF DESCRIPTION OF THE DRAWINGS

These and other features, aspects, and advantages of the present invention will become better understood with regard to the following description, appended claims and accompanying figures where:

Figure 1:
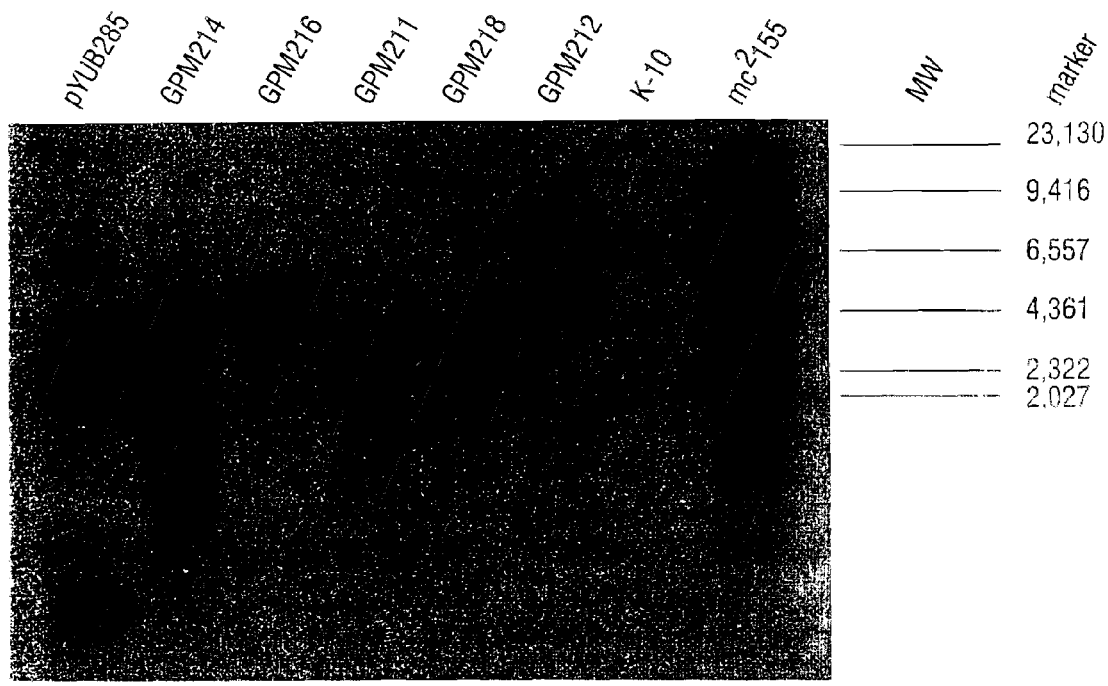
FIG. 1 shows Southern blot analysis of *M. paratuberculosis* K-10 true transposon mutants.

ABBREVIATIONS AND DEFINITIONS cfu=colony forming unit pfu=plaque forming unit MIC=minimal inhibitory concentration "Albumin dextrose complex" means 2 g glucose, 5 g bovine serum albumin fraction V and 0.85 g NaCl in 100 mL deionized water.

As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications for example, labels, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified fowls of the polynucleotide. Polynucleotides include both sense and antisense strands.

As used herein "polypeptide", "protein" and "peptide" are used interchangeably and refer to a polymer of two or more amino acids. Included within the definition are polypeptides containing one or more analogs of an amino acid, including, for example, unnatural amino acids, polypeptides with substituted linkages, as well as modifications known in the art, both naturally occurring and non-naturally occurring.

As used herein, the term "animal" includes human beings.

As used herein, the term "patient" includes humans and animals.

DETAILED DESCRIPTION OF PREFERRED EMBODIMENT

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application are herein incorporated by reference in their entirety as if each individual publication, patent, patent application, database or other reference were specifically and individually indicated to be incorporated by reference.

The present invention relates to the method for identification of virulence determinants in bacteria particularly in members of the genus *Mycobacterium*. The genus *Mycobacterium* includes the species *M. phlei, M. smegmatis, M. africanum, M. fortuitum, M. marinum, M. ulcerans, M. tuberculosis, M. bovis, M. microti, M. avium, M. paratuberculosis, M. leprae, M. lepraemurium, M. intracellulare, M. scrofulaceum, M. xenopi, M. genavense, M. kansasii, M. simiae, M. szulgai, M. haemophylum, M. asiaticum, M. amlmoense*, and *M. shimoidei*. In one embodiment, the mycobacteria are slow growing mycobacteria. Any virulent strain of a species of *mycobacterium* that is slow growing and capable of being maintained in vitro can be used in the practice of the present invention. Examples of slow growing mycobacteria include *M. tuberculosis, M. bovis, M. africanum, M. marinum, M. avium*, and *M. paratuberculosis*. In one embodiment, strains of *M. paratuberculosis* are used and in particular the virulent strain K-10 of *M. paratuberculosis*.

Once a particular strain or strains has been chosen, mutations are introduced into the genome of the selected bacteria. Numerous means for inserting mutations into the genome of bacteria are known in the art and can be found in standard references such as Sambrook et al. *Molecular Cloning*, 2nd ed., Cold Spring Harbor Press, 1989 and Ausubel et al., *Short Protocols in Molecular Biology*, 3rd ed., Wiley, 1995. A discussion of methods of mutagenesis directed particularly to mycobacteria can be found in Jacobs et al., *Methods in Enzymology*, 204:537-555, 1991 and Pelicic et al., *Molec. Microbiol.*, 28:413-420, 1998. Mutations introduced can be site directed to a particular gene or sequence of interest, or the location of the mutations can be random. If random mutation is used, it is preferred that the mutations be approximately evenly distributed throughout the genome. Two particularly useful forms of mutagenesis are allelic exchange mutagenesis and transposon mutagenesis although other forms of mutagenesis such as chemical and enzymatic (e.g. restriction enzyme mediated integration) mutagenesis can be used.

In allelic exchange mutagenesis, the gene or sequence of interest is disrupted using homologous recombination such that the functional allele is replaced with an inactivated copy. Following introduction of the inactivated copy, the virulence of the transformed bacteria can be compared to the parental strain. The efficiency of allelic exchange mutation is improved through the use of counter selection strategies which eliminate transformants retaining the delivery vector. Successful allelic exchange mutations have been achieved in mycobacteria (U.S. Pat. No. 6,096,549; Balasubramanian et al., *J Bacteriol.* 178:273-279, 1996; McFadden. *Molec. Microbiol.*, 21:205-211, 1996; Pelicic et al., *Proc. Natl. Acad. Sci. USA*, 94:10955-10960, 1997).

In one embodiment, the introduction of mutations is by transposon mutagenesis. Transposon mutagenesis occurs by the insertion of a mobile element called a transposon into the gene or sequence of interest, thus disrupting its function. An advantage of transposon mutagenesis is that no previous assumptions need to be made regarding the identity of the gene or sequence to be disrupted. In general, a transposon contains an inverted repeat sequence at the 5' and 3' ends and a gene or genes encoding transposase enzyme(s) between the inverted repeats. In transposon mutagenesis, the transposon is removed from a vector and inserted or transposed into the chromosome of a bacteria to be mutated. As used herein, the term "transposon" is a general term and encompasses both non-mutated and mutated transposons. Thus, the term includes transposons in which a portion of the nucleotide sequence has been deleted and/or replaced, and/or wherein the transposon contains additional DNA sequences. Transposon mutagenesis has been successfully used in mycobacteria (Martin et al., *Nature*, 345:739-743, 1990; Guilhot et al., *J Bacteriol.* 176:535-539, 1994; Pelicic et al., *Proc. Natl. Acad. Sci USA*, 94:10955-10960, 1997; Bardarov et al., *Proc. Natl. Acad. Sci. USA*, 94:10961-10966, 1997). In one preferred embodiment, transposon mutagenesis is accomplished by use of the transposable element Tn5367, a single-unit transposon which carries a kanamycin-resistance marker and the *M. smegmatis* insertion sequence IS 1096 (Cirillo et al., *J. Bacterol.* 173:7772-7780, 1991; McAdam et al., *Infect. Immunol.*, 1004-1012, 1995).

Introduction of vectors useful in the practice of the present invention can be accomplished by any suitable method known in the art. Various methods are known for the introduction of DNA into bacterial cells and include, for example, calcium phosphate transfection, DEAE-dextran mediated transfection, Polybrene, protoplast fusion, liposomes, phage infection, conjugation, and electroporation. Commonly, introduction of vectors for allelic exchange or transposon mutagenesis in mycobacteria is by either electroporation or phage infection. In one preferred embodiment, introduction of the DNA is by phage infection and in particular by the use of the TM4 thermosensitive transposon delivery shuttle plasmid phAE94 (Bardarov et al. *Proc. Natl. Acad. Sci. USA*, 94:10961-10966, 1997).

In general, a shuttle plasmid comprises a bacteriophage DNA into which a plasmid sequence has been inserted into a nonessential region. In one embodiment, the bacteriophage is from a mycobacteriophage and the plasmid sequence is a cosmid sequence, preferably an *E. coli* cosmid sequence. Shuttle plasmids can, therefore, replicate in bacteria as a plasmid/cosmid or as a phage. The inserted plasmid/cosmid DNA is preferably flanked by restriction sites not found in the bacteriophage DNA, so that the inserted DNA can be easily excised. In one embodiment, a cosmid containing a transposon is obtained and inserted into the bacteriophage backbone using standard methods of cosmid cloning (Sambrook et al., *Molecular Cloning*, 2nd ed., Cold Spring Harbor Press, 1989).

The sequence containing the transposon can, and usually does, also contain a selection marker sequence. Typically, this sequence encodes a protein necessary for the survival or growth of the host cell transformed with the shuttle plasmid. Examples of suitable markers for prokaryotic cells include tetracycline, kanamycin, and ampicillin resistance.

In one embodiment, the shuttle plasmid is a temperature sensitive plasmid. Temperature sensitive shuttle plasmids are those which replicate and form plaques at a permissive temperature, but do not undergo a lytic cycle and so do not form plaques at a non-permissive temperature.

Once the temperature sensitive shuttle plasmid has been produced it can be introduced into a bacterial host which will allow growth of the shuttle plasmid as a lytic bacteriophage at a permissive temperature. Introduction of the shuttle plasmid into the host cell can be by any method suitable for the introduction of DNA into a bacterial host including those discussed above. Introduction of the shuttle plasmid and culture at a permissive temperature results in the production of large numbers of bacteriophage particles. The bacteriophages are isolated using standard techniques and then used to infect susceptible bacteria at a non permissive temperature. At the non-permissive temperature, rather than causing lysis of the infected bacteria, the shuttle plasmid gives rise to bacterial transductants which can then be selected on the basis of a selection marker, if present.

In one preferred embodiment, introduction of the DNA is by the use of the TM4 thermosensitive transposon delivery shuttle plasmid phAE94 (Bardarov et al. *Proc. Natl. Acad. Sci. USA*, 94:10961-10966, 1997). This shuttle plasmid contains the transposon Tn5367 which is a derivative of the insertion sequence IS1096 from *M. smegmatis* and carries the aph gene conferring kanamycin resistance. In this embodiment, phAE94 is propagated in *M. smegmatis* at a permissive temperature and the resulting mycobacteriophage used to infect susceptible mycobacteria at a non-permissive temperature. *Mycobacteria* undergoing transformation are then selected by kanamycin resistance.

Once one or more mutations have been introduced into the genome, a selection method is employed in order to select those bacteria which the mutation has disrupted a gene or nucleic acid sequence potentially involved in virulence. Various methods can be employed to determine virulence. For example, suitable host animals can be inoculated with the mutated bacteria and monitored for development of disease symptoms and/or replication of the organisms injected. Alternatively, selection can be based on the use of a chemical, and in particular, an antimicrobial, the effect of which is associated with a trait related to virulence. Since bacterial growth is a necessary part of virulence, in one embodiment the selection is based on the ability of an antimicrobial to kill growing mycobacteria while having a reduced or no effect on non-growing bacteria. Thus, antimicrobials that interfere with processes involved in bacterial growth and in particular DNA replication are preferred. Although not necessary to practice the present invention, it is preferred that the antimicrobial agent used be able to enter eukaryotic cells, thus allowing screening of transformed bacteria in intracellular culture systems, e.g. macrophage culture. In one embodiment, the antimicrobial is a quinolone. In another embodiment, the antimicrobial is a fluoroquinolone. In yet another embodiment, the antimicrobial is Bay y 3118. Bay y 3118 has been reported to kill growing but not non-growing *Mycobacterium avium* within human macrophages (Bermudez et al., *FEMS Microbial. Lett.* 1787:19-26, 1999). In still another embodiment, the antimicrobial is D-cycloserine (Cáceres et al., *J. Bacteriol.* 179:5046-5055, 1997).

The exact amount of the antimicrobial used will vary with the particular substance and organism in question. In general, the concentration of the antimicrobial should exceed the approximate minimal inhibitory concentration (MIC) for the particular organism being studied. Determination of MIC is routine in the art and can be accomplished by the skilled technician without undue experimentation. In one embodiment, in which *M. paratuberculosis* strain K-10 and Bay y 3118 are used, the MIC is approximately 0.015 μg/mL. In another embodiment, the concentration of Bay y 3118 is 5× the MIC. In still another embodiment in which *M. paratuberculosis* strain K-10 and D-cycloserine are used the MIC is approximately 25 μg/mL. In yet another embodiment, the concentration of D-cycloserine is 5× the MIC.

In general, screening is accomplished by culturing the mutated bacteria in the presence of the antimicrobial agent. As will be apparent to those skilled in the art, the exact culture conditions will vary with the organism being studied, When *M. paratuberculosis* is used, either broth or macrophage culture can be used. Methods for the culture of mycobacteria are well known in the art and can be found, for example, in Jacobs et al., *Methods in Enzymology,* 204:537-555, 1991; Foley-Thomas et al. *Microbiology* 141:1173-1181, 1995; and Williams et al., *J. Clin. Microbiol.* 37:304-309, 1999. In one embodiment, mycobacteria are grown in Middlebrook 7H9 broth. As is known in the art and described in the references cited above, Middlebrook 7H9 broth is supplemented depending on the particular species of mycobacteria cultured. Alternatively, an intracellular culture system such as a macrophage or amoeba (Cirillo et al., *Infect. Immunol.* 65:3759-3767, 1997) culture system can be used. *Mycobacteria* naturally infect macrophages as part of the disease process. Thus, mycobacteria can be cultured in macrophages. In this system, mycobacteria, preferably in a single cell suspension, are added to a culture of macrophages from a suitable species. The macrophages used can be recently collected from blood using known, standard methods or can be from a macrophage cell line. The mycobacteria are allowed to infect the macrophages. The infected macrophages are then maintained under suitable culture conditions so that the mycobacteria survive and grow within the macrophages.

The antimicrobial selection agent is added to the culture system at a concentration that exceeds the MIC and the culture continued for a period of time sufficient to kill the multiplying bacteria. It will be apparent to those skilled in the art that the exact amount of time required will vary with such well known factors as the amount and type of selection agent used, the culture system, and the species of mycobacteria. In general, the selection conditions can be optimized by culturing bacteria for various times and at various concentrations of antimicrobials to determine the combination of times and concentrations which effectively kill growing, but not non-growing bacteria. Such optimization can readily be achieved by the skilled technician without undue experimentation. After the selection period, the surviving bacteria are collected, individual bacteria isolated, by for example clonal streaking, and the clones expanded using standard culture methods. If desired following expansion, the selected bacteria can be further characterized by genetic, biochemical, and animal testing.

Characterization can include determination of whether the transposon has been incorporated into the genome. This can be accomplished using well known techniques such as Southern blotting, dot or slot blots, and in situ hybridization to bacterial chromosomes, using a polynucleotide probe complimentary to the transposon used. Information regarding the location of the transposition and the gene or sequence disrupted can be obtained by sequencing. In general, this can be accomplished by obtaining purified genomic DNA from transfected bacteria and cutting the DNA with restriction enzymes that do not cut within the transposon. The restriction fragments obtained can be cloned into a cloning vector using standard techniques and amplified for sequencing. Any known method of sequencing can be used. In one embodiment, sequencing is accomplished by cycle sequencing outward from the transposon. Once the sequence information has been obtained, the nucleic acid sequences or deduced amino acid sequences can be compared to sequences in publicly available databases such as those maintained by the National Center for Biotechnology Information at http://www.ncbi.nlm.nih.gov/, the European Bioinformatics Institute at http://www.ebi.ac.uk/, The Institute for Genomic Research at http://www.tigr.org, The Sanger Centre at http://www.sanger.ac.uk/Projects/, The Computational Biology Center of the University of Minnesota Microbial Genome Project at http://cbc.umn.edu/, and the Institute Pasteur at http://genolist.pasteur.fr/. Based on sequence homology, the identity of the gene or sequence disrupted by the insertion can be determined and thus the virulence determinant identified.

Alternatively or additionally information can be obtained by biochemical studies, especially by auxotrophic analysis. Auxotrophic mutants are mutants that require a nutrient or substance not required by the parent organism from which the mutant was derived. Determination of auxotrophic mutants can be made by comparing growth on complete and incomplete growth medium. For those mutants showing no or reduced growth on incomplete medium, the missing nutrients can be individually added back until growth comparable to that seen with complete medium is obtained. Methods for selecting auxotrophic mutants are well known in the art and can be accomplished by the skilled technician without undue experimentation.

Whether the selected mutants lack virulence can be tested by inoculating susceptible animals with the selected organism and determining if the organism results in clinical symptoms or if the organism multiples and spreads beyond the site of inoculation. The animal inoculated can be the natural host for the organism or it can be a animal model. In one embodiment, the mouse model and in particular the beige mouse (Whipple et al. *Proc. 3rd Intl. Colloq Paratuberculosis*, Intl. Assn. Paratuberculosis, pp. 551-552) is used for virulence testing. In general, the animal is inoculated with a quantity of the organism sufficient to result in infection. Inoculation can be oral, parenteral or any other suitable method. The exact amount of the organism inoculated will vary with well known factors such as the species, size and age-of the animal. Determination of the proper quantity of organism to be administered can be determined by one of ordinary skill in the art without undue experimentation. At various times after inoculation, the animals are sacrificed and various organs examined for the presence of the organism. If the organism is not detected, it can be assumed that the gene or sequence disrupted is a virulence determinant.

Confirmation that the sequence identified is a virulence determinant can be obtained by a complementation study. In a complementation study, the wild type sequence is reintroduced into the mutated organism, for example by introduction of an expression vector, and the effect on virulence determined. If the disrupted sequence is associated with virulence, replacement of the sequence should restore virulence. In general, the disrupted gene or sequence is inserted into a suitable expression vector using standard techniques in molecular biology found in standard references and described herein. The expression vector is then introduced into the mutant organism and the virulence of the complemented organism is tested as described above.

The method of the present invention can be used to create strains of mycobacteria which are non-virulent or have reduced virulence. As used herein the term attenuated refers to mutated strains whose virulence is reduced as compared to the same organism in its non-mutated form. Such attenuated mycobacteria can be used in compositions for the treatment and/or prophylaxis of diseases caused by or associated with the organism. This includes compositions designed to stimulate an immune response against a organism, for example, a vaccine. Attenuated strains produced by the method of the present invention are thought to be particularly useful because they make it possible to differentiate between individuals who test positive for the presence of mycobacteria due to vaccination or natural infection based on the presence of the introduced transposon.

Likewise, polypeptides encoded by sequences identified by the method of the present invention as being involved in virulence can be used to stimulate an immune response in an animal. In this embodiment, the sequence identified as described herein is placed into an expression vector. If desired, the polypeptide sequence identified can be fused or assembled with additional amino acids to form a fusion protein. Such fusion proteins can be used to increase the solubility or antigenicity of the virulence polypeptide. Methods for the production of fusion proteins are well known in the art and can be found in standard molecular biology references. The expression vector is, in turned, introduced into a suitable prokaryotic or eukaryotic host cell and the encoded polypeptide expressed. The resulting polypeptide is then purified using standard biochemical techniques from lysates of the host cells or from culture medium containing the host cells.

The compositions can be administered to any animal which can become infected with a species of mycobacteria. In one embodiment, the animal is a ruminant animal, more preferably a Bovidae and more preferably still a member of the genus *Bos*. When the composition comprises whole mycobacteria, the bacteria can be live or they can be killed by any suitable means such as heating, chemical treatment, or disruption of the bacterial cell. Bacteria can be in a preserved state such as in a lyophilized form which may or may not be reconstituted prior to administration. The compositions can comprise attenuated bacteria alone, virulence polypeptides alone, or a combination of attenuated bacteria and virulence polypeptides.

The compositions of the present invention can be administered by a variety of routes and methods. Suitable routes and methods of administration include orally, parenterally, by inhalation spray, rectally intradermally, transdermally, or topically in dosage unit formulations containing conventional nontoxic pharmaceutically acceptable carriers, adjuvants, and vehicles as desired. The term parenteral as used herein includes subcutaneous, intravenous, intramuscular, or intrasternal injection, or infusion techniques. In one embodiment, the complexes are administered by injection. In another embodiment, the compositions are administered orally. In yet another embodiment, the compositions are administered by inhalation. Methods for the formulation of drugs is well known in the art and is discussed in, for example, Hoover, John E., *Remington's Pharmaceutical Sciences*, Mack Publishing Co., Easton, Pa. (1975), and Liberman, H. A. and Lachman, L. Eds., *Pharmaceutical Dosage Forms*, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compositions discussed herein can be prepared by mixing the active agent with a suitable non-irritating excipient such as cocoa butter, synthetic mono-, di-, or triglycerides, fatty acids, or polyethylene glycols which are solid at ordinary temperatures, but liquid at the rectal temperature, and which will therefore melt in the rectum and release the composition.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of attenuated organism and/or virulence determinants that can be combined with the carrier materials to produce a single dosage form will vary depending upon the patient or animal and the particular mode of administration. Compositions of the present invention can be given as a single administration or in multiple administrations over a period of time. If desired, after the initial administration or series of administrations, additional periodic administrations (e.g. boosters) of the composition can be given.

The attenuated organisms and/or virulence determinants can be administered in combination with a pharmaceutically acceptable immune system stimulant or adjuvant. Examples of such immune system stimulants or adjuvants include, but are not limited to, Alum (aluminum phosphate or aluminum hydroxide), Freund's adjuvant, calcium phosphate, beryllium hydroxide, dimethyl dioctadecyl ammonium bromide, saponins, polyanions, e.g. poly A:U, Quil A, inulin, lipopolysaccharide endotoxins, liposomes, lysolecithins, zymosan, propionibacteria, mycobacteria, and cytokines, such as, interleukin-1, interleukin-2, interleukin-4, interleukin-6, interleukin-12, interferon-α, interferon-γ, granulocyte-colony stimulating factor.

In another embodiment, the virulence determinants identified by the method of the present invention are used for diagnosis of mycobacterial infection. Biological samples can be obtained from a subject suspected of suffering from a mycobacterial infection. Biological samples include any sample of tissue or fluid isolated from an individual. Examples of biological samples, include, but are not limited to plasma, serum, spinal fluid, lymph fluid, sections of skin, respiratory, intestinal, and genitourinary tracts, tears, saliva, mucus, milk, blood cells, tumors, tumor cells, and organs. Biological samples also include samples obtained from in vitro cell culture, for example, cells grown in culture, including putatively infected cells and recombinant cells, cell components, and conditioned media resulting from the culture of cells in culture medium.

In one embodiment, diagnosis is made based on the presence of polynucleotide sequences identified by the method of the present invention. In this embodiment, a biological sample which contains nucleic acids is obtained from an individual. Polynucleotides whether in the form of DNA or RNA are obtained from the sample using well established techniques which are known to those in the art and can be found in standard molecular biology references; such as those cited herein. In one embodiment, diagnosis is made based on hybridization of specific polynucleotide probes to sequences encoding virulence determinants identified by the present invention. Probes should be of sufficient length to provide specificity. In general, probes are at least 4 nucleotides in length, more preferably at least 8 nucleotides in length, even more preferably at least 12 nucleotides in length, and more preferably still at least 20 nucleotides in length. Probes used can be obtained from mycobacteria using standard methods, for example, by the use of restriction enzyme digestion to obtain suitable nucleic acid fragments which are then inserted into a cloning vector, which is in turn introduced into a suitable host cell. The host cells are then grown under conditions allowing replication of the cloning vector, and the desired sequences isolated and used as probes. Alternatively, probes can be produced by chemical synthesis in automated systems by any suitable method, for example, the phosphoramidite method of Beaucage and Carruthers (*Teta. Letts.*, 22:1859-1862, 198). When used for hybridization, it is desirable that the probes be completely complementary to the sequence to be detected, but probes which exhibit only partial complementarity can be used. Hybridization probes can, and often do, contain detection moieties. Such detection moieties include, but are not limited to radioactive labels, such as radionuclides, fluorophores or fluorochromes, peptides, enzymes, vitamins and steroids.

In order to insure specificity hybridizations should be conducted under highly stringent conditions. As is recognized in the art stringency is a combination of many factors such as temperature and the composition of the hybridization and wash solutions. Thus, many different conditions can result in the same degree of stringency. In general, highly stringent conditions are achieved by hybridization in a solution of 6×SSC or SSPE at a temperature 20-25° C. below the melting temperature ($T_m$) for DNA-DNA hybrids and 10-15° C. below the $T_m$ for DNA-RNA hybrids followed by washing in 0.1×SSC or SSPE at 42° C. Even higher stringency conditions can be achieved by washing in 0.1×SSC or SSPE at 50-65° C.

In situations where the amount of nucleic acid which can be obtained from the sample is small, it may be desirable to amplify the sequences of interest by methods such as the polymerase chain reaction (PCR), the ligase chain reaction (LCR) (see, Wu and Wallace, *Genomics*, 4:560-569, 1989; Landegren et al., *Science*, 241:1077-1080, 1988), transcription amplification (Kwoh et al., *Proc. Natl. Acad. Sci. USA*, 86:1173-1177, 1989), self-sustained sequence replication (Guatelli et al., *Proc. Natl. Acad. Sci. USA*, 87:1874-1878, 1990), and nucleic acid based sequence amplification (NASBA). In one preferred embodiment, amplification is by PCR. Optimization of conditions for conducting PCR must be determined for each reaction and can be accomplished without undue experimentation by one of ordinary skill in the art. In general, methods for conducting PCR can be found in U.S. Pat. Nos. 4,965,188, 4,800,159, 4,683.202, and 4,683,195; Ausbel et al., eds., *Short Protocols in Molecular Biology*, 3$^{rd}$ ed., Wiley, 1995; and Innis et al., eds. *PCR Protocols*, Academic Press, 1990.

Diagnosis of infection by the presence of sequences identified by the method of the present invention can be achieved by visualization of PCR products of a characteristic size. Individuals testing positive due to natural infection can be differentiated from individuals who have received attenuated vaccine by the presence of the transposon which will result in an increase in the size of the amplification product. Alternatively, the amplification products could be detected by hybridization to specific probes as described above.

In another embodiment, diagnosis is made by detection of polypeptides encoded by the sequences identified by the method of the present invention. In one embodiment, such detection is by an immunological assay. Various immunological assays known in the art can be used, including but not limited to competitive and non-competitive assay systems using techniques such as radioimmunoassays, ELISA (enzyme linked immunosorbent assay), “sandwich” immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

Antibodies, either polyclonal or monoclonal, against polypeptides identified by the method of the present invention for use in immunological assays can be produced by known methods. If polyclonal antibodies are desired, an animal is immunized with a virulence polypeptide identified by the method of the present invention. The composition used for immunization can comprise the polypeptide alone or may further comprise an adjuvant or other immune system stimulant. Further, the polypeptide can be conjugated to a carrier molecule or be part of a fusion protein in order to increase antigenicity. Following immunization, serum is collected from the immunized animals and treated according to well established methods. If desired, the antibody can be purified using known techniques such as affinity chromatography. Methods for the production of polyclonal antibodies are well known in the art and can be found for example in Ausubel et al., *Short Protocols in Molecular Biology,* 3rd ed. Wiley, 1995.

Likewise, monoclonal antibodies can be produced using well known techniques. In general, immortal antibody producing cell lines are created by cell fusion, direct transformation of B lymphocytes with oncogenic DNA, or transfection of Epstein-Barr virus. Panels of hybridomas can then be screened for the production of suitable monoclonal antibodies using standard techniques. Methods for the production of monoclonal antibodies are well known in the art and can be found for example in U.S. Pat. Nos. 4,341,761; 4,399,121; 4,427,783; 4,444,887; 4,466,917; 4,472,500; 4,491,632; and 4,493,890.

Also encompassed by the present invention are diagnostic kits. Such kits can contain probes, primers and/or antibodies for the detection of polynucleotides or polypeptides identified by the method of the present invention. The probes, primers and antibodies may, optionally, incorporate a detection moiety such as those described herein. The kits may further comprise buffers, reagents and instructions necessary for the use of the contents of the kits to detect the presence of the polynucleotides and/or polypeptides.

EXAMPLES

Example 1

Bacterial Strains, Growth Conditions, and Recombinant DNA

A virulent clinical isolate of *M. paratuberculosis* (strain K-10) was used. *M. paratuberculosis* cultures were grown standing at 37° C. in a complete growth medium comprising Middlebrook 7H9 broth enriched with oleic acid albumin dextrose complex, 0.4% casamino acids containing vitamins 40 μg/mL L-tryptophan, 0.5 μg/mL mycobactin J (Allied Monitor, Fayette, Mo.), and 0.05% Tween 80. *Escherichia coli* DH5α cells, used as cloning hosts were grown on Luria-Bertani (LB) agar or broth supplemented with 50 μg/mL kanamycin. The conditionally replicating (temperature sensitive) recombinant mycobacteriophage phAE94 (Bardarov et al., *Proc. Natl. Acad. Sci. USA,* 94:10961-10966, 1997) used to deliver the transposon Tn5367 (McAdam et al., *Infect. Immun.* 63:1004-1012, 1995) was propagated in *Mycobacterium smegmatis* $mc^2155$ at 30° C. as has been described previously. (Bardarov et al. *Proc. Nat. Acad. Sci. USA,* 94:10961-10966, 1997). The transposon Tn5367 is a derivative of the insertion sequence IS1096 from *M. smegmatis* and carries the aph gene conferring kanamycin resistance.

Example 2

Transposon Mutagenesis

*M. paratuberculosis* cultures were grown to approximately $1.5\times10^8$ cfu/mL ($OD_{600}$ 0.38-0.75). Cultures (50 mL) were concentrated by centrifugation and resuspension in 1 mL of MP buffer (50 mM Tris-HCL, pH 7.6, 150 mL NaCl, 2 mM $CaCl_2$). Bacterial cells and phage were incubated at a non-permissive temperature (37° C.) at the ratios and for the times indicted in Table 1. After completion of the adsorption time, 2 mL of prewarmed stop buffer (MP buffer containing 20 mM sodium citrate and 0.2% Tween 20) was added to prevent further phage infections. Kanamycin resistant ($kan^r$ olonies were selected on complete growth medium without Tween plus 15 g/L agar containing 50 μg/mL kanamycin at 37° C. In five independent experiments, 5,620 transductants were obtained (Table 1). In further experiments, the number of transductants was increased to 13,526. This provides a representation of approximately 95% of the genome. Probability (%) values for the representation of the mutant pool were calculated using the formula $\ln(1-P)=N\times\ln(1-1/4500)$ assuming a genome size of 5.0 Mb (allowing a 5% underestimation error for the reported size) and 4500 target genes and where N=13479 for P=95%.

To verify that transposition events had occurred in these mutants, genomic DNA was isolated using standard techniques (Sambrook et al., *Molecular Cloning*, 2nd ed., Cold Spring Harbor Press, 1989) and digested with PstI which does cleave the transposon. The digests were then hybridized overnight under stringent conditions of 65° C. in Rapid-hyb buffer (Amersham-Pharmacia, Piscataway, N.J.) using radiolabeled plasmid pYUB285 which carries the transposon as a probe followed by two, 20 minute washes in 2×SSC at 28° C., a 15 minutes wash in 0.5×SSC at 65° C. and a final 15 minute wash in 0.1×SSC at 65° C. Each mutant gave, as expected, one hybridizable band with at least four distinct sizes observed (FIG. 1). This confirmed that transpositions had occurred and that each transformant represented transpositions at different chromosomal locations. Furthermore all mutants gave the same pattern of IS900 hybridizable bands as expected for derivatives of strain K-10, and none of the samples hybridized with TM4 DNA indicating that hybridization was not due to the residual presence of vector phage DNA.

Example 3

Subcloning and DNA Sequencing

Figure 2:
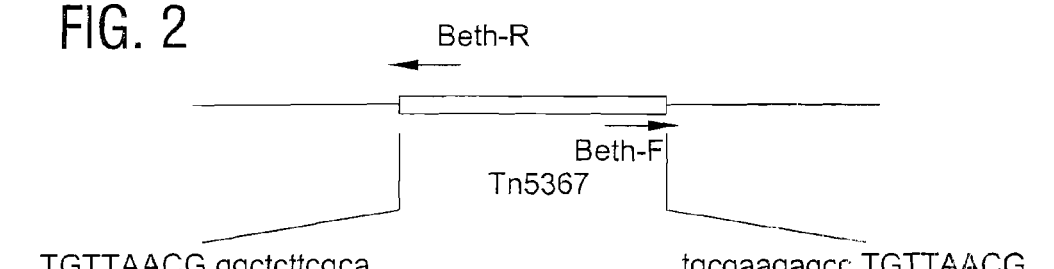
FIG. 2 shows the location of the BETH-R and BETH-F primers in the Tn5367 on and partial results of sequencing. Also shown is the alignment of nucleotide sequence obtained from mutant GPM207 (SEQ ID NO: 5) using BETH-F and the xerC gene (GenBank No. Z97369) (SEQ ID NO: 6).
Figure 3A:
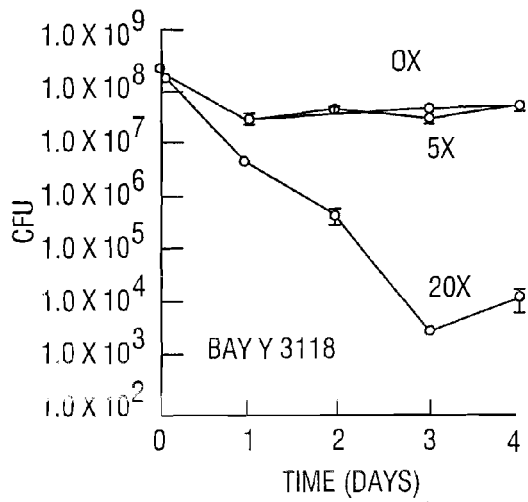
FIG. 3 shows the effects of co-culture with either Bay y 3118 or D-cycloserine on growing and non-growing *M. paratuberculosis* strain K-10 in complete Middlebrook 7H9 medium.
Figure 3B:
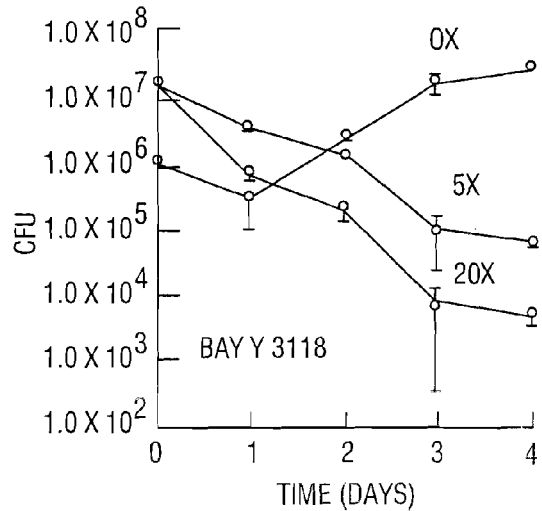
Figure 3C:
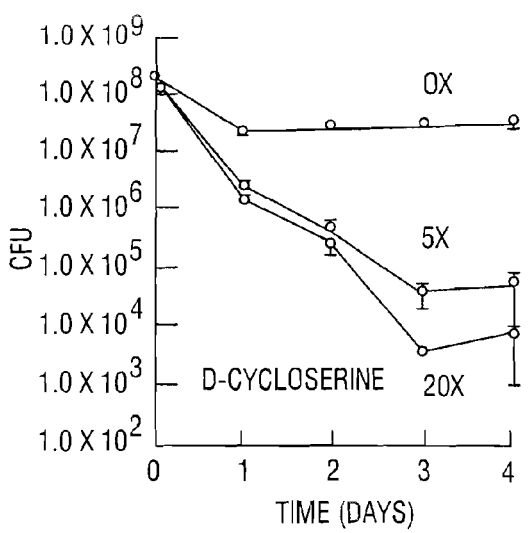
Figure 3D:
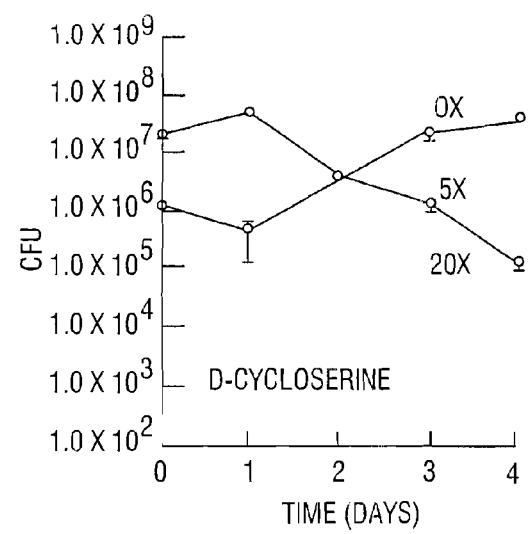

Chromosomal DNA from transposon mutant GPM207 and pACYC184 vector DNA was digested with EcoRI, ligated into the corresponding EcoRI site in the pACYC184 vector and transformed into *E. coli* DH5α cells by using standard methods (Ausubel et al., *Short Protocols in Molecular Biology*, 3rd ed., Wiley 1995). *E. coli* were cultured as described above and kanamycin resistant transformants isolated. Plasmid DNA was isolated from selected transformants and subjected to automated sequencing using the BigDye Terminator Cycle Sequencing Ready Reaction (Perkin Elmer) and the ABI Prism 310 Genetic Analyzer (Perkin Elmer). Chromosomal DNA sequences at the junctions of the transposon insertions were obtained by cycle sequencing outward from the transposon using the primers 5'-GGTCAGCGCAGGC-GAAGCCC (BETH-F, SEQ ID NO: 1) and 5'-GCCAGGTC-CACACTGCCCCC (BETH-R, SEQ ID NO: 2). The results are shown in FIG. 2. An 8 by duplication was observed at the transposon-chromosomal junction (SEQ ID NOS: 3 & 4) (FIG. 2). This duplication was also reported by Pelicic et al. (*Proc. Natl. Acad. Sci. USA*, 94:10955-10960, 1997) for transpositions of this element into five different genes in *M. bovis* BCG. The nucleotide sequence derived from BETH-F was translated based on the mycobacterial codon usage. A BLAST search identified the chromosomal gene carrying the transposon insertion as homologous to the *M. leprae* xerC gene (GenBank No. Z97369; SEQ 113 NO: 6) encoding a putative integrase/recombinase (52% identity and 63% similarity for the region sequenced, see FIG. 2).

Example 4

Susceptibility of Growing and Non-Growing Populations of *M. paratuberculosis* in Broth Culture to Antimicrobial Agents Antimicrobial agents (antibiotics) tested were the fluoroquinolone Bay y 3118, and D-cycloserine. The aminoglycoside amikacin which kills both growing and non-growing *M. paratuberculosis*, was included as a control. *M. paratuberculosis* strain K-10 was grown in complete Middlebrook 7H9 medium containing mycobactin J as described above to an optical density ($OD_{600}$) of 0.3 to 0.4. For non growing conditions, cells (200 ml) were harvested at room temperature, washed in MSS (Middlebrook 7H9 salt solution: 1.0 g/L $KH_2PO_4$, 0.05 g/L $MgSO_4$, $NH_4SO_4$, 2.5 g/L $Na_2HPO_4$, 0.0005 g/L $CaCl_2$, 0.001 g/L $ZnSO_4$, and 0.001 g/L $CuSO_4$), and resuspended in MSS as a single-cell suspension (Williams et al., *J. Clin. Microbiol.*, 37:304-309, 1999). Aliquots (10 ml at a cell density of $2\times10^8$ CFU/mL) were placed in sterile tissue culture flasks, and antibiotics were added at the following final concentrations Bay y 3118: 0.075 µg/mL (5×MIC) and 0.3 µg/mL (20×MIC); D-cyloserine: 125 µg/mL (5×MIC) and 500 µg/mL (20×MIC); amikacin: 10 µg/mL (5×MIC), and 40 µg/mL (20×MC). These cultures and a control without antibiotics (0x) were incubated at 37° C. and appropriate dilutions were plated in triplicate onto complete Middlebrook 7H9 medium at various time points. When these cells were inoculated into complete Middlebrook medium (growing conditions), they displayed normal growth (growth control). For growing conditions, cells were treated as described except that the growth control (0x) was diluted 1:10 and all cells were washed and resuspended in complete medium instead of MSS. The cells were also inoculated into MSS (no-growth control).

The results are shown in FIG. 3 and show that Bay y 3118 at 5× the MIC does not kill non growing bacteria, but has a bactericidal action on growing bacteria. At both 5× and 20× the MIC, D-cycloserine had a moderate bactericidal effect on both growing and non growing bacteria. Amikcin, as expected, was bactericidal for both growing and non growing bacteria, but bacteria in stasis were particularly more susceptible.

Example 5

Susceptibility of Growing and Non-Growing Populations of *M. paratuberculosis* in Macrophage Culture to Antimicrobial Agents Bovine macrophages of the BOMAC line (Stabel and Stabel, *Vet. Immunol. Immunopathol.*, 45:211-220, 1995) are infected with single-cell suspensions of mutated bacteria as described in Example 4 at a MOI of 10:1. Infected BOMAC cells are then incubated at 39° C. in RPMI-1640 tissue culture medium containing Bay y 3118 at 5× the MIC for three days. After the incubation period, the infected BOMAC cells are lysed with 0.25% SDS and the viable bacteria recovered by centrifugation. These bacteria are used to infect a fresh culture of BOMAC cells, and this procedure is repeated until each pool of mutants has been passed 3 times through BOMAC cells. The bacteria recovered from the final passage and sample from earlier passages are then subjected to molecular characterization as described in Example 3.

Example 6

Virulence Testing of *M. paratuberculosis* in Susceptible Mice

Groups of 6 to 8 week old beige mice were infected orally with non mutated (wild type) *M. paratuberculosis* strain K-10 and euthanized at various times post infection. Bacterial loads in liver, spleen and ileum were determined. Intestinal wall tissue was fixed and stained with hematoxylin and eosin for histological assessment. Mice were given either a high infectious dose of 5 doses of $1\times10^8$ bacteria administered on alternate days (Experiment I) or a low infectious dose of $1\times10^4$ bacteria in a single dose (Experiment II). The results are given in Table 2. With the high infectious dose, the bacteria continued to grow in the spleen during the 8-week period but bacterial load in the liver leveled off at three weeks. Effective multiplication during the 8-week period was also observed in the terminal ileum with an in vivo generation time of about one week. These results showed that *M. paratuberculosis* can infect beige mice through the intestinal mucosa. A higher multiplication in the liver and spleen as compared to the ileum, however, indicated that the mice were experiencing a systemic infection. Thus, using the high infectious dose, beige mice infected with *M. paratuberculosis* did not parallel all the features of ruminant paratuberculosis. Under the conditions of Experiment II, the ileum displayed the greatest bacterial load. Bacterial multiplication continued in all three organs for the 8-week period. Thus, using a lower dose, oral infection of beige mice with *M. paratuberculosis* followed a course similar to the more time consuming monoassociated nude mouse intragastric model (Hamilton et al., *Vet Pathol.* 28:146-155, 1991).

Example 7

Virulence Tested of Mutated Bacteria in Susceptible Mice

Beige mice are inoculated orally with a single dose of $1 \times 10^4$ bacteria as described in Example 6. For each mutant tested there is a test group of mice that receives the mutated organism and a positive control group that receives the non mutated parental (wild type) strain from which the mutated organisms are derived. At various times after inoculation, animals are euthanized and bacterial loads in liver, spleen and ileum are determined as described in Example 6. Mutant strains which do not show continued multiplication in tissues as compared to the corresponding controls are considered to be non-virulent.

Example 8

Screening of Mutant Bacteria for Ability to Stimulate Immunity

Mutant bacteria which have been found to be non virulent by the method of Example 7 are tested to determine their ability to stimulate immunity against subsequent infection with non-mutated, virulent strains. Beige mice are inoculated orally with mutant non-virulent strains as described in Example 6. A second group of mice acts as a control group and receives only vehicle. At various times after inoculation, mice are challenged with $1 \times 10^4$ bacteria of the non-mutated virulent parental strain. At various times after challenge mice are euthanized and bacterial loads in liver, spleen and ileum are determined as described in Example 6. Mutated strains which are found to confer immunity are further tested to determine optimal dosage rates and methods of immunization, for example, single or multiple administration oral versus parenteral administration.

TABLE 1

| Expt.[1] | $OD_{600}$ culture[2] | Ration Ph/B[3] | Ads Time (hours)[4] | Transd. Freq.[5] | Transp Freq[6] | Kan[r] mutants[7] | N[8] | P value[9] |
|---|---|---|---|---|---|---|---|---|
| I | 0.48 | 20 | 4 | $5.4 \times 10^{-8}$ | $1.0 \times 10^{-6}$ | 1344 | 1344 | 26% |
| II | 0.48 | 200 | 4 | $5.1 \times 10^{-9}$ | $9.8 \times 10^{-7}$ | 1275 | 2619 | 42% |
| III | 0.38 | 25 | 6 | $7.0 \times 10^{-9}$ | $1.8 \times 10^{-7}$ | 176 | 2795 | 46% |
| IV | 0.38 | 25 | 24 | $5.4 \times 10^{-9}$ | $1.4 \times 10^{-7}$ | 136 | 2931 | 48% |
| V | 0.75 | 350 | 4 | $1.1 \times 10^{-9}$ | $3.6 \times 10^{-5}$ | 2689 | 5620 | 71% |

[1]Experiment number
[2]$OD_{600nm}$ of *M. paratuberculosis* at harvest
[3]Ratio of phAE94 PFU at 30° C. to the number of *M. paratuberculosis* K-10 CFU
[4]Adsorption time in hours at 37° C.
[5]Transduction frequency: number of kanamycin-resistant colonies obtained at 37° C. per infecting phage particle.
[6]Transposition frequency: number of kanamycin-resistant colonies obtained at 37° C. per recipient cell.
[7]Total number of kanamycin-resistance colonies obtained at 37° C. (putative transposon mutants)
[8]Cumulativce number of kanamyucin-resistant colonies obtained
[9]Probability (%) value for the representation of the mutant pool assuming randon transposition.

TABLE 2

| | CFU/g (mean of all mice in group ± SEM) | | | | | |
|---|---|---|---|---|---|---|
| | Liver | | Spleen | | Ileum | |
| Week | I | II | I | II | I | II |
| 1 | $5.9 \pm 0.6 \times 10^7$ | $7.9 \pm 0.4 \times 10^1$ | $2.7 \pm 0.3 \times 10^7$ | $1.6 \pm 0.3 \times 10^2$ | $3.5 \pm 0.6 \times 10^4$ | $5.9 \pm 0.6 \times 10^3$ |
| 2 | $1.4 \pm 0.8 \times 10^8$ | $1.5 \pm 0.5 \times 10^1$ | $1.1 \pm 0.4 \times 10^8$ | $1.8 \pm 0.4 \times 10^2$ | $4.0 \pm 0.3 \times 10^4$ | $2.2 \pm 0.2 \times 10^4$ |
| 3 | $2.5 \pm 0.4 \times 10^8$ | Not done | $1.7 \pm 0.5 \times 10^8$ | Not done | $9.9 \pm 0.6 \times 10^4$ | Not done |
| 4 | Not done | $3.0v0.2 \times 10^2$ | Not done | $1.6 \pm 0.3 \times 10^2$ | Not done | $2.5 \pm 0.2 \times 10^4$ |
| 8 | $2.9 \pm 0.6 \times 10^8$ | $1.1 \pm 0.6 \times 10^3$ | $5.6 \pm 0.4 \times 10^8$ | $5.9 \pm 0.4 \times 10^3$ | $2.2 \pm 0.3 \times 10^5$ | $1.3 \pm 0.3 \times 10^4$ |

CONCLUSION

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the are in light of the foregoing examples and detailed description. Accordingly, this invention is intended to embrace all such alternatives modifications, and variations that fall within the spirit and scope of the following claims.

What is claimed and desired to be secured by Letters Patent is a follows:

1. A method for isolating a bacteria comprising:
   introducing at least one mutation into the genome of a virulent bacteria;
   culturing the mutated bacteria in the presence of an antimicrobial agent that kills growing but not non-growing bacteria;
   selecting surviving bacteria;
   testing the selected surviving bacteria for virulence; and
   selecting attenuated mutant bacteria.
2. The method of claim 1, wherein said bacteria is a mycobacteria.
3. The method of claim 1, wherein said antimicrobial agent is a fluoroquinolone.
4. The method of claim 3, wherein said fluoroquinolone is Bay y 3118.
5. The method of claim 1, wherein said antimicrobial is D-cycloserine.
6. The method of claim 1, wherein said mutation is introduced by insertion of a transposon.
7. The method of claim 1, wherein said mutation is a random mutation.
8. A composition consisting of an attenuated mutant bacteria selected by the method of claim 1, said composition capable of stimulating an immune response against a disease caused by the virulent bacteria.
9. The composition of claim 8, further comprising a pharmaceutically acceptable carrier, diluent or excipient.
10. The composition of claim 8, wherein said bacteria is a mycobacteria.

* * * * *